(12) United States Patent
Soares et al.

(10) Patent No.: US 8,038,641 B2
(45) Date of Patent: Oct. 18, 2011

(54) TOOLS AND METHODS FOR PROGRAMMING AN IMPLANTABLE VALVE

(75) Inventors: Brian M. Soares, Norton, MA (US); LiJuan He, Bolton, MA (US); Allison H. Bedwinek, Boston, MA (US); Kyle Jarger, Stow, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 379 days.

(21) Appl. No.: 12/415,590

(22) Filed: Mar. 31, 2009

(65) Prior Publication Data

US 2010/0249690 A1 Sep. 30, 2010

(51) Int. Cl.
*A61M 5/00* (2006.01)
*F61K 31/00* (2006.01)

(52) U.S. Cl. .................. 604/9; 251/65; 251/292

(58) Field of Classification Search .............. 604/8, 9; 251/65, 292

See application file for complete search history.

(56) References Cited

U.S. PATENT DOCUMENTS

| 4,443,214 | A | 4/1984 | Marion |
| 4,676,772 | A * | 6/1987 | Hooven ........................ 604/9 |
| 5,643,194 | A | 7/1997 | Negre |
| 7,921,571 | B2 * | 4/2011 | Moureaux et al. ........ 33/355 R |
| 2005/0092335 | A1 | 5/2005 | Bertrand |
| 2005/0279960 | A1 | 12/2005 | Cabaud |
| 2007/0093714 | A1 | 4/2007 | Beaucoup |

FOREIGN PATENT DOCUMENTS

| EP | 136054 A2 | 4/1985 |
| FR | 2354103 A1 | 1/1978 |
| WO | WO 0054826 A1 | 9/2000 |
| WO | WO 2005092424 A1 | 10/2005 |
| WO | WO 2009034410 A1 | 3/2009 |

OTHER PUBLICATIONS

European Search Report EP10250658.1, dated Jul. 6, 2010.

* cited by examiner

*Primary Examiner* — Leslie Deak (57) ABSTRACT

A two-part tool for reading and adjusting an implantable valve, and methods of use. The tool includes a locator-indicator component that, when placed matingly on the patient's skin over the valve, provides magnetic reading of the valve setting. The tool also includes an adjustor component that couples to the locator-indicator component and is rotatable to change a valve setting.

25 Claims, 5 Drawing Sheets

TOOLS AND METHODS FOR PROGRAMMING AN IMPLANTABLE VALVE

FIELD OF THE INVENTION

The invention relates generally to surgically implantable fluid drainage systems. More specifically, the invention relates to extracorporeal tools for reading and setting adjustable valves used for cerebrospinal fluid drainage.

BACKGROUND OF THE INVENTION

Hydrocephalus is a neurological condition caused by the abnormal accumulation of cerebrospinal fluid (CSF) within the ventricles, or cavities, of the brain. Hydrocephalus, which can affect infants, children and adults, arises when the normal drainage of CSF in the brain is blocked in some way. Such blockage can be caused by a number of factors, including, for example, genetic predisposition, intraventricular or intracranial hemorrhage, infections such as meningitis, or head trauma. Blockage of the flow of CSF consequently creates an imbalance between the rate at which CSF is produced by the ventricular system and the rate at which CSF is absorbed into the bloodstream. This imbalance increases pressure on the brain and causes the ventricles to enlarge. Left untreated, hydrocephalus can result in serious medical conditions, including subdural hematoma, compression of the brain tissue, and impaired blood flow.

Hydrocephalus is most often treated by surgically inserting a shunt system to divert the flow of CSF from the ventricle to another area of the body, such as the right atrium, the peritoneum, or other locations in the body where CSF can be absorbed as part of the circulatory system. Various shunt systems have been developed for the treatment of hydrocephalus. Typically, shunt systems include a ventricular catheter, a shunt valve and a drainage catheter. At one end of the shunt system, the ventricular catheter can have a first end that is inserted through a hole in the skull of a patient, such that the first end resides within the ventricle of a patient, and a second end of the ventricular catheter that is typically coupled to the inlet portion of the shunt valve. The first end of the ventricular catheter can contain multiple holes or pores to allow CSF to enter the shunt system. At the other end of the shunt system, the drainage catheter has a first end that is attached to the outlet portion of the shunt valve and a second end that is configured to allow CSF to exit the shunt system for reabsorption into the bloodstream. Typically, the shunt valve is palpatable by the physician through the patient's skin after implantation.

Shunt valves, which can have a variety of configurations, can be designed to allow adjustment of their fluid drainage characteristics after implantation. It is generally preferred to enable external adjustment of the pressure threshold to avoid invasive surgical procedures each time an adjustment is required. In some shunt systems, the shunt valve contains a magnetized rotor to control the pressure threshold of the valve. Physicians can then use an external adjustment mechanism, such as a magnetic programmer containing a powerful magnet, to adjust the pressure threshold of the shunt valve. One issue with magnetically programmable valves is a potential for unintentionally adjusting the valve by the misapplication of an external magnetic field. Unintentional adjustment of the valve could lead to either the overdrainage or underdrainage of CSF, which can result in dangerous conditions, such as subdural hematoma. For example, the direction of physical approach to the valve by a magnetic programmer, or an inappropriate initial rotational orientation of a magnetic programmer with respect to the valve, has the potential to inadvertently change a setting of the valve.

It is also important to be able to externally read or verify the setting of the valve. With some adjustable valves, x-ray images are used to determine the current setting of the valve, before and after adjustment. With other adjustable valves, the orientation of the rotor in the valve can be read magnetically, using a magnetic compass-like device positioned above the valve, outside the skin of the patient.

Although tools and methods exist for adjusting CSF shunt valve settings, as do other tools and methods for reading a valve setting, a need exists for magnetically programmable valve systems having reduced probability of unintentional adjustment, as well as for tools and methods that provide both adjustment and verification of implantable valve settings.

SUMMARY OF THE INVENTION

Accordingly, the present invention provides unified tools and methods for externally reading and changing a setting of a magnetically adjustable, implantable valve.

One aspect of the invention is a tool for reading and changing a setting of an implantable valve. In various embodiments, the tool is used with a valve that controls fluid flow or pressure, and can be a CSF drainage control valve. The valve has an external cross section and an internal magnetic rotor with an associated magnetic field. The tool includes a locator-indicator having opposed upper and lower surfaces. A shaft extends from the upper surface. The shaft has a longitudinal axis that is substantially perpendicular to the upper surface and in an embodiment, the shaft is rotationally coupled to the upper surface, and the locator-indicator includes markings that indicate the relative rotational orientation of the shaft with respect to the upper surface.

The lower surface of the locator-indicator includes a biased recess having an internal cross-section matingly complementary to the external cross section of the valve. The biased recess is adapted to be positioned in proximity to the valve, on the skin of the patient over the implanted valve, in a unique rotational orientation about the axis. In this position, the axis extends through the rotor of the valve.

The locator-indicator includes a magnetic indicator that can be used to read the rotational orientation of the rotor, and thereby the setting of the valve. In an embodiment, the indicator is rotatably mounted about the axis between the upper and the lower surface and can rotate into alignment with the rotor under influence of the rotor's magnetic field. The tool also includes a magnetic adjustor that can be slid onto the shaft along the axis. The adjustor has a strong magnetic field for rotating the rotor about the axis in response to rotation of the adjustor about the axis. Thus, rotating the adjustor about the axis can be used to change the setting of the valve, for example, a pressure or flow control setting.

Another aspect of the present invention is tool for reading and changing a current setting of a magnetically readable and settable valve that has been implanted in a patient, where the valve has a physical shape and orientation that are palpatable through the skin of the patient. The tool includes a housing having a lower surface and an upper surface. The lower surface has a physical shape complementary to the palpatable shape so that when the tool is placed over the valve on the skin of the patient, it can be oriented to match the orientation of the valve beneath the skin.

A shaft extends substantially perpendicularly from the upper surface of the housing, one end of the shaft being coupled to the upper surface. In an embodiment, the shaft is rotatable about an axis oriented substantially perpendicular to the upper surface. The coupling between the rotatable shaft and the upper surface can provide one or more of audible, visible, or tactile feedback to a user when it is rotated with respect to the upper surface into any of a number of predetermined rotational positions about the axis, for example, eight positions.

The tool includes a disk at least partially contained and rotatably mounted within the housing. The disk can be free to rotate about the axis, or a mechanical lock can be set to prevent the disk from rotating freely. When the lower surface of the tool is in place on the palpatable shape and no mechanical lock is engaged, the disk, in the manner of a compass needle, is magnetically self-aligning to a rotational orientation of the valve, indicative of the current valve setting. The disk bears at least one visible marking indicating the disk's rotational orientation about the axis, and the upper surface can include a window for viewing the at least one mark.

The tool further includes a magnetic element slidably and removably mountable onto the shaft, along the axis. The magnetic element can be disk-shaped and include a central aperture for receiving the shaft. Further, the aperture and the shaft can be rotationally keyed to one another so that the magnetic element can be slid onto the shaft in only one rotational orientation and, when the magnetic element is rotated about the axis, the shaft rotates along with it. The magnetic element is capable of changing the setting of the valve when the magnetic element is mounted on the shaft and rotated about the axis. The tool can also be adapted so that it cannot change the valve setting if the magnetic element it is not mounted to the shaft, for example, if is further away from the upper surface than the length of the shaft. The tool can also include markings that display the valve setting as determined by the rotational orientation of the magnetic element about the axis.

Yet another aspect of the present invention is a method for reading and changing a current setting of a magnetically readable and settable valve implanted in a patient. The valve has a physical shape and orientation that is palpatable through the skin of the patient. In the method, a first tool portion is provided, the first portion having an upper surface and a lower surface. The lower surface is adapted to matingly fit over the palpatable shape on the patient. The first portion includes a magnetic indicator for reading a setting of the valve. A shaft extends from the upper surface, the shaft having an axis. The first portion of the tool is positioned matingly in proximity to the palpatable shape on the patient, with the shaft extending in a direction substantially away from the patient. With the first portion of the tool in place over the palpatable shape, the current valve setting is read using the magnetic indicator.

A second tool portion is also provided, the second tool portion adapted to removably slide over the shaft to mate with the first portion. The second portion includes a magnet adapted to change the setting of the valve when the second portion is rotated about the axis. The second portion is slid over the shaft, along the axis, to mate with the first portion. Once mated with the first portion, the second portion is rotated about the axis to change the valve setting to a desired new setting. The second portion of the tool can then be slid away and removed from the first portion, and the new valve setting can be verified using the magnetic indicator.

BRIEF DESCRIPTION OF THE DRAWINGS

This invention is described with particularity in the appended claims. The above and further aspects of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

FIG. 3A through FIG. 3C illustrate another embodiment of a two-component tool according to the present invention.

FIG. 4 through FIG. 6D illustrate an embodiment of a method for reading and setting an implanted, magnetically adjustable valve using a tool of the present invention.

DETAILED DESCRIPTION

Tools and methods of the present invention enable a physician to consistently and reliably read and change a setting of (that is, "adjust") an implantable, magnetically settable valve ("valve"). The valve includes a magnetic rotor that is rotatable about a rotor axis by an externally applied magnetic field, to adjust the valve from a current setting to a target setting. In an exemplary embodiment, the valve is implanted under a patient's scalp and used to control at least one of CSF drainage flow and pressure for a patient with hydrocephalus.

Figure 1:
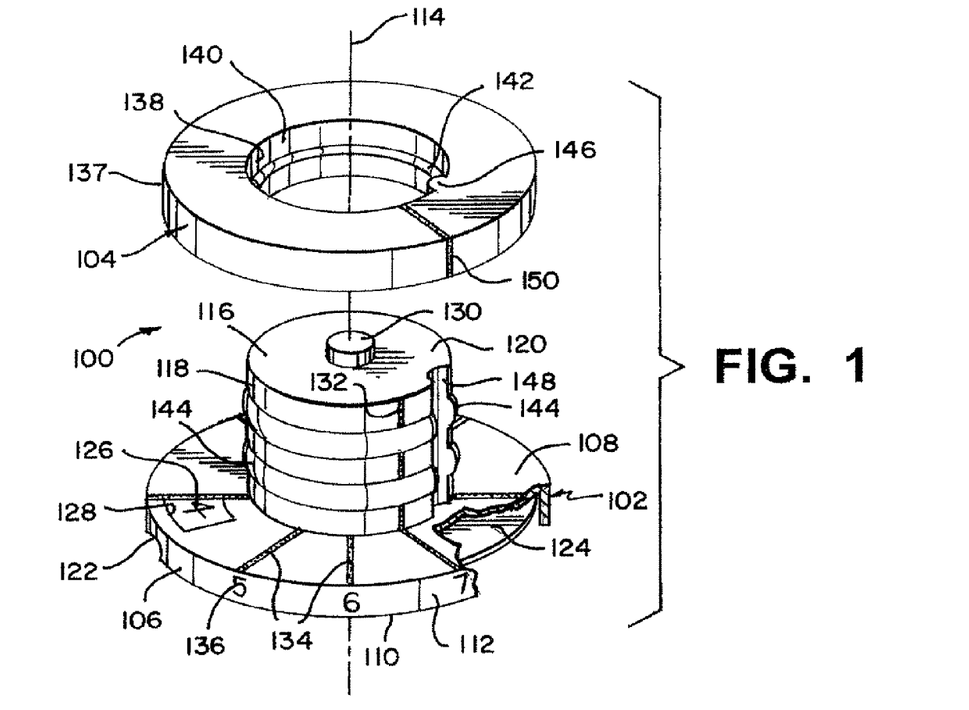
FIG. 1 is a perspective view illustrating an embodiment of a two-component tool according to the present invention.
Figure 2:
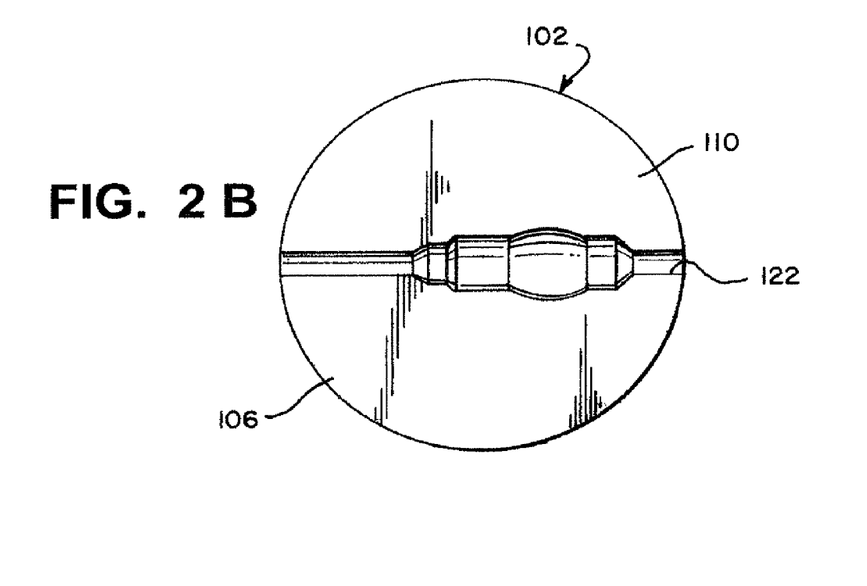
FIG. 2A is a top view illustrating the two components of the tool of FIG. 1.
FIG. 2B is a bottom view of the locator-indicator component of the two component tool illustrated FIG. 1
Figure 2A:
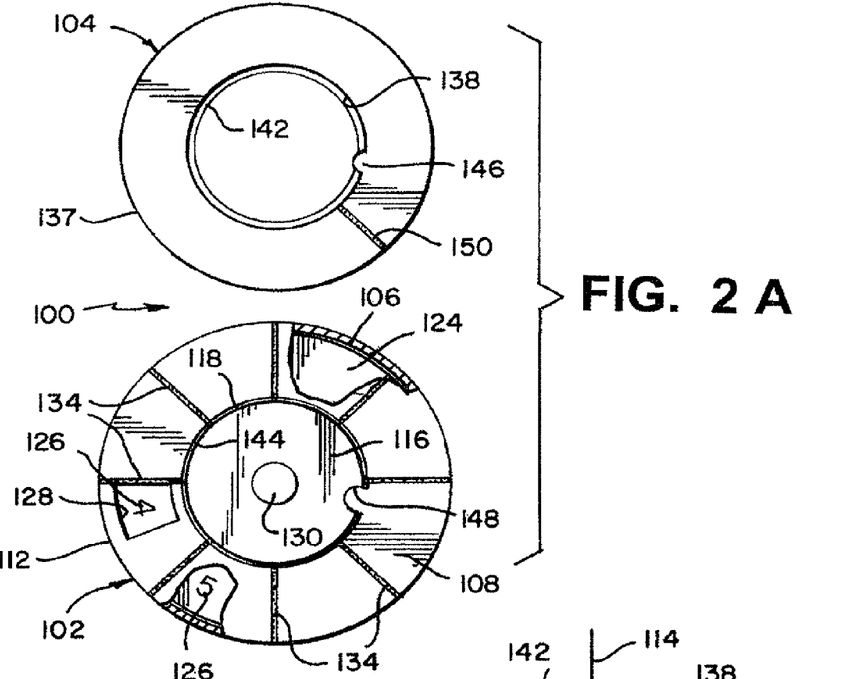

Referring more particularly to the figures, FIG. 1 illustrates in perspective view, an embodiment of a two-component tool 100 of the present invention. The tool 100 includes a locator-indicator component 102 and an adjustor component 104. FIG. 2a illustrates top views of the locator-indicator component 102 and the adjustor component 104, and FIG. 2b illustrates a bottom view of the locator-indicator component 102. The locator-indicator component 102 comprises a housing 106 having an upper surface 108, a lower surface 110, and a substantially cylindrical outer surface 112 having a central tool axis 114. A shaft 116 having an outer shaft surface 118 extends along the tool axis 114 from the upper surface 108 of the housing 106. The shaft 116 terminates at a shaft end 120 and has a longitudinal shaft length between the upper surface 108 and the shaft end 120. In an embodiment, the outer shaft surface 118 is substantially cylindrical in cross section about the tool axis 114. In another embodiment, the outer shaft surface 118 is substantially polygonal in cross section about the tool axis 114.

Figure 4:
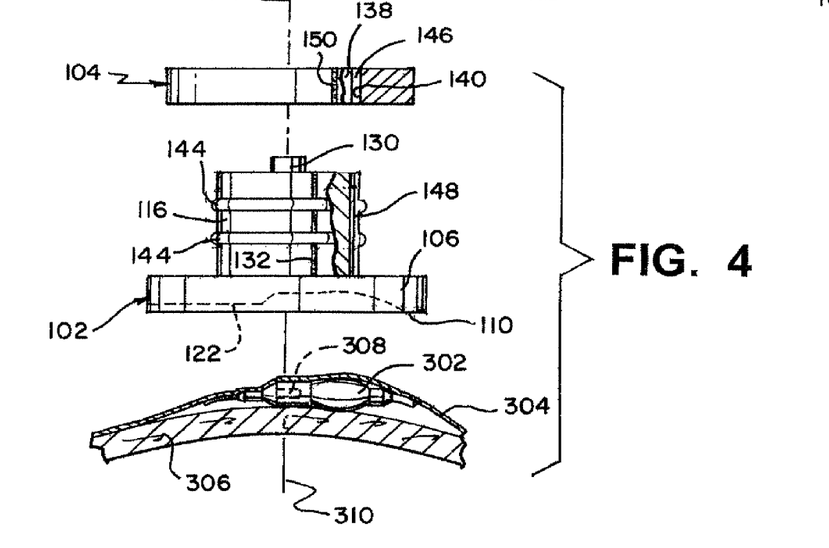

The lower surface 110 includes a biased recess 122. The biased recess 122 is adapted to be matingly complementary in shape to the valve (not illustrated in FIG. 1, FIG. 2a, or FIG. 2b, but illustrated in dashed lines in FIG. 4), preferably as palpatable through the patient's scalp. We use the term "biased" herein to mean that the recess 122 has a noncircular cross section that can be positioned matingly on the scalp above the implanted valve, only in a predetermined position on the scalp and in a unique rotational orientation about the tool axis 114. Further, the locator-indicator component 102 is adapted for the tool axis 114 to align through the rotational axis of the magnetic rotor of the valve when the biased recess 122 is positioned matingly on the scalp over the valve. In an embodiment, the palpatable shape closely corresponds to a manufactured shape of the valve, which can be any of a variety of shapes.

Enclosed substantially within the housing 106 is a magnetic reading disk 124 rotatably mounted about the tool axis 114. The reading disk 124 is provided with a circumferentially distributed plurality of markings 126 associated with a corresponding plurality of settings of the valve. In an embodiment, the upper surface 108 of housing 106 is optically opaque and includes a window 128 through which only one of the plurality of markings 126 is visible, as illustrated in FIGS. 1 and 2a. The plurality of settings of the valve corresponds to a plurality of rotational orientations of the magnetic rotor in the valve. In one embodiment, the plurality of markings 126 comprises eight equally spaced markings positioned at angular intervals of 45 degrees on an upper surface of the reading disk 124. In another embodiment, the plurality of markings 126 comprises numeric markings. It is to be understood that any number of valve settings and corresponding markings of any type is intended to be included within the scope of the present invention.

The reading disk 124 is magnetic, its magnetic field having a predetermined rotational orientation about the tool axis 114 with respect to the plurality of markings 126. The reading disk 124 can be fabricated from a magnetic material, or can be fabricated substantially from a non-magnetic material, with one or more magnet mounted thereto or incorporated therein to provide the predetermined orientation. The reading disk 124 is mounted for rotation about the tool axis 114 in the manner of rotation of a magnetic compass needle in response to an external magnetic field, and can rotationally orient itself to the magnetic orientation of the magnetic rotor when placed in proximity thereto. The reading disk 124 is too weakly magnetic to adjust the valve. In an embodiment, the one of the plurality of markings 126 visible through the window 128 indicates the valve setting.

In an embodiment, the reading disk 124 is mechanically restrained from freely rotating about the tool axis 114 except when a release mechanism is activated. The disk can be mechanically restrained by any type of mechanism that releasably prevents free rotation of the reading disk 124. In one embodiment, the reading disk 124 is restrained from rotating by a resiliently-loaded mechanical linkage comprising a component that can be moved away from the reading disk 124 by manually pressing a resiliently loaded pushbutton 130. Activating the release mechanism releases the reading disk 124 to rotate freely about the tool axis 114, to align with the magnetic field of the rotor. The pushbutton 130 can be provided anywhere on the surface of the locator-indicator component 102 that provides convenient access for activation by a user of the tool 100. In the embodiment illustrated in FIG. 1 embodiment, the pushbutton 130 is positioned on the shaft end 120.

In one embodiment, the shaft 116 is rotatably mounted to the housing 106 so that the shaft 116 can be rotated about the tool axis 114 with respect to the housing 106, to any one of a plurality of preferred rotational orientations corresponding to the plurality of settings of the valve. In a further embodiment, a visible mark is 132 provided on the outside shaft surface 118 as a rotational position reference, and the housing 106 is provided with one or more indicator for each of the plurality of preferred rotational orientations. The one or more indicator can be any type of positional indicator, including but not limited to radial markings 134 on a surface of the housing 106, numbers 136 or other symbols on a surface of the housing 106, detents or other means to provide visual, tactile or auditory feedback such as clicking sounds, as the shaft 116 is rotated into a preferred orientation.

The adjustor component 104 is seen to comprise a disk 137 having a generally circular external cross section and a substantially central aperture 138 having an interior surface 140 adapted to slidingly fit over the shaft 116, for releasably mounting the adjustor component 104 onto the locator-indicator component 102. In another embodiment, the external cross section of the adjustor component 104 is polygonal. In an embodiment, the interior surface 140 includes a physical feature 142 that can be a raised ring, an o-ring or another feature, that is adapted to engage with one or more corresponding physical features 144 on the outside shaft surface 118 to provide positive positioning, for example, a releasable "snap-fit" of the adjustor component 104 onto the shaft 116. The corresponding physical features 142, 144 of this embodiment are illustrated in FIG. 1 only. Positive positioning provides both a repeatable axial location of the adjustor component 104 along the shaft 116 during valve adjustments, and a secure docking location for the adjustor component 104 during storage of the tool 100 between uses.

In one embodiment, the aperture 138 and the shaft 116 are rotationally keyed to one another using a keying feature 146 on the adjustor component 104 and a complementary keying feature 148 on the shaft 116. In this embodiment, an alternate visible mark 150 can be provided on the adjustor component 104 to supplement or substitute for the visible mark 132 on the shaft 116. With the adjustor component 104 mounted to the locator-indicator component 102, the adjustor component 104 can be rotated about the tool axis 114. In embodiments including rotational keying between the adjustor component 104 and the shaft 116, the shaft 116 rotates along with the adjustor component 104 with respect to the housing 106 when the adjustor component 104 is rotated about the tool axis 114.

The adjustor component 104 is magnetic, providing a strong enough magnetic field to rotate the rotor about the tool axis 114 and thereby change the valve setting from a current setting to a target setting when the adjustor component 104, mounted on the locator-indicator component 102 (in proximity to the rotor), is rotated about the tool axis 114. During rotation, one of both of the visible mark 132 and the alternate visible mark 150 is referenced to the one or more indicator 134, 136 to identify the target rotational setting and thereby adjust the valve to the target setting.

Figure 3A:
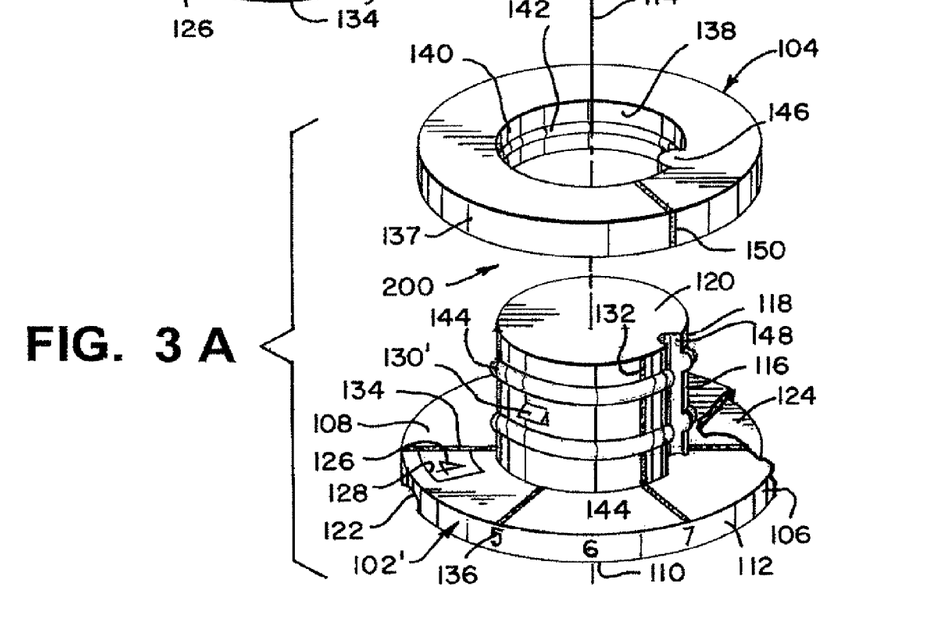
Figure 3B:
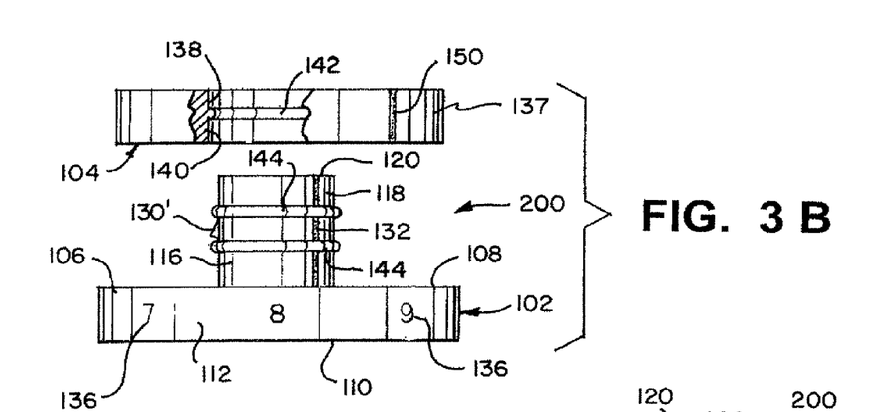
Figure 3C:
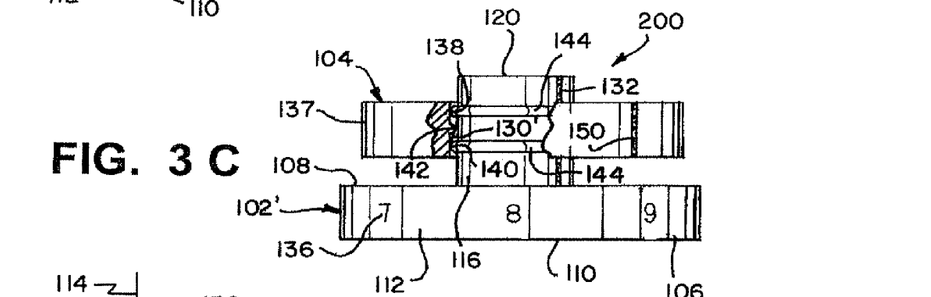

In an alternate embodiment 200 illustrated in FIG. 3a, an alternate locator-indicator component 102' comprises an alternate release pushbutton 130' positioned on the outside shaft surface 118. In this embodiment, in addition to the alternate pushbutton 130' being adapted for manual activation, axially mounting the adjustor component 104 to the locator-indicator component 102' depresses the alternate pushbutton 130' to activate the release mechanism, freeing the disk reading 124 to rotate into orientation with the magnetic field of the adjustor component 104. Now referring to FIG. 3b, as the adjustor component 104 is axially slid 202 onto the shaft 116, the alternate pushbutton 130' is seen to be depressed, as illustrated in FIG. 3c, when engaged by the interior surface 140. Freeing the reading disk 124 to rotate into orientation with the strong magnetic field of the adjustor component 104 when these two components are in close proximity to one another reduces the potential for the relatively strong magnetic field of the adjustor component 104 to permanently modify the orientation of the much weaker magnetization of the reading disk 124.

In another embodiment, the adjustor component 104 and the locator-indicator component 102 are not rotationally keyed together, and the adjustor component 104 is free to rotate on the shaft 116, about the axis tool 114. In this embodiment, the alternate visible mark 150 on the adjustor component 104 is referenced to the one or more indicator 134, 136 during adjustment of the valve. In yet another embodiment, the locator-indicator component 102 includes the biased recess 122 and the shaft 116, but does not include means to read the valve.

A method for reading and adjusting an implanted magnetic valve using the two-component tool 100 according to the present invention is illustrated schematically in FIG. 4 through FIG. 6d. First referring to FIG. 4, in preparation for a valve reading and adjustment, the two-component tool 100 comprising the locator-indicator component 102 and the adjustor component 104 is provided for adjusting a valve 302 that has previously been implanted between the scalp 304 and the skull 306 of a patient. The valve 302 includes a magnetic rotor 308 that can be rotated about a rotor axis 310 in response to an externally applied magnetic field, to adjust the valve 302. The biased recess 122 is seen to be adapted to be matingly complementary in shape to the valve 302, preferably as palpatable through the scalp 304.

The valve 302 is seen to have a non-circular cross section about the rotor axis 310, and the rotor 308 is seen to be not centrally positioned within the valve 302. This asymmetry ensures that the biased recess 122 can be positioned matingly over the valve 302 on the scalp 304 only in a unique rotational orientation about the rotor axis 310. The release button 130 is seen not to be activated (not depressed) in FIG. 4, so the reading disk 124 is not free to rotate about the axis 114, and the setting of the valve is not being read.

Figure 5A:
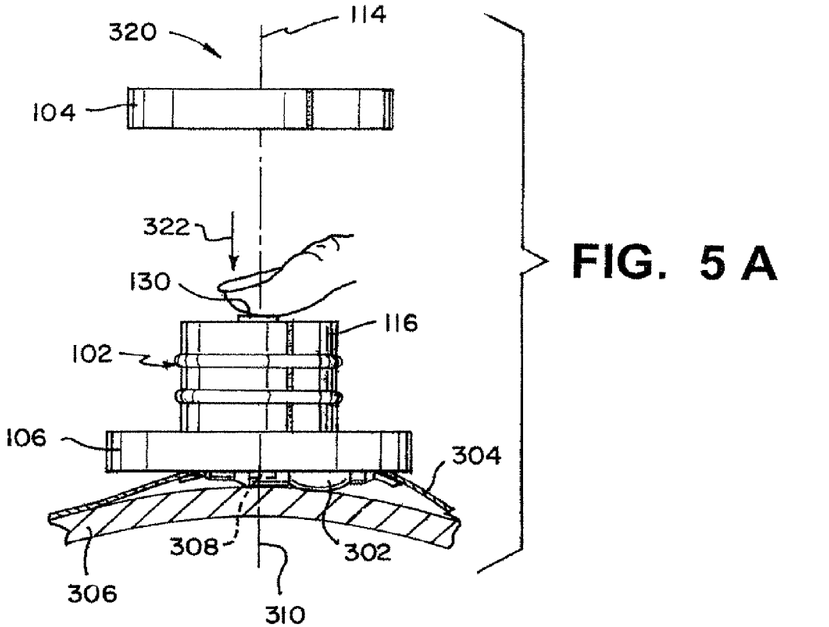

Now referring to FIG. 5a, in locating and indicating steps 320, the locator-indicator component 102 is seen to have been positioned substantially on the scalp 304 above the valve 302, to matingly fit the biased recess 122 on the scalp 304, over the valve 302. With the biased recess 122 matingly positioned over the valve 302, the tool axis 114 is seen to be substantially collinear with the rotor axis 310. This alignment supports both accurate reading and adjustment of the valve 308. Additionally, the biased recess 122 fits over the valve 302 in a single rotational orientation about the axis 114, thus ensuring that angle-dependent markings on the tool 100 are uniquely oriented about the axis 114 with respect to the valve 302.

Further, the release pushbutton 130 is seen in FIG. 5a to be pressed 322, freeing the reading disk 124 to rotate about the axis 114 to align with the magnetic field of the rotor 308, thereby providing a reading of the current setting of the valve 302. In an embodiment, the pushbutton 130 is pressed 322 for several seconds to obtain a stable reading, then released, to provide stable viewing of the current setting of the valve 308, with the reading disk 124 rotationally locked.

Figure 5B:
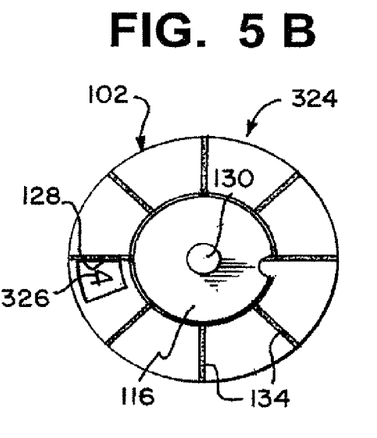
Figure 5C:
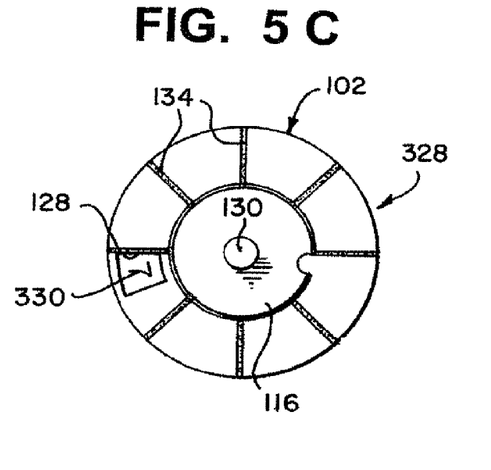

In an example of reading the valve 302, FIG. 5b illustrates a top view 324 of the locator-indicator component 102, before the pushbutton 130 is pressed. A first one 326 of the plurality of markings 126 on the disk 124 is seen to be visible through the window 128. The first one 326 of the markings 126 does not represent a reading of the valve 302. FIG. 5c illustrates the top view of the locator-indicator component 102, after 328 the pushbutton 130 has been pressed 322, and the disk 124 has rotated into alignment with the magnetic field of the rotor 308. A second one 330 of the plurality of markings 126 on the disk 124 is now seen to be visible through the window 128, corresponding to the current reading of the valve 302.

Figures 6A, 6B, 6C, 6D:
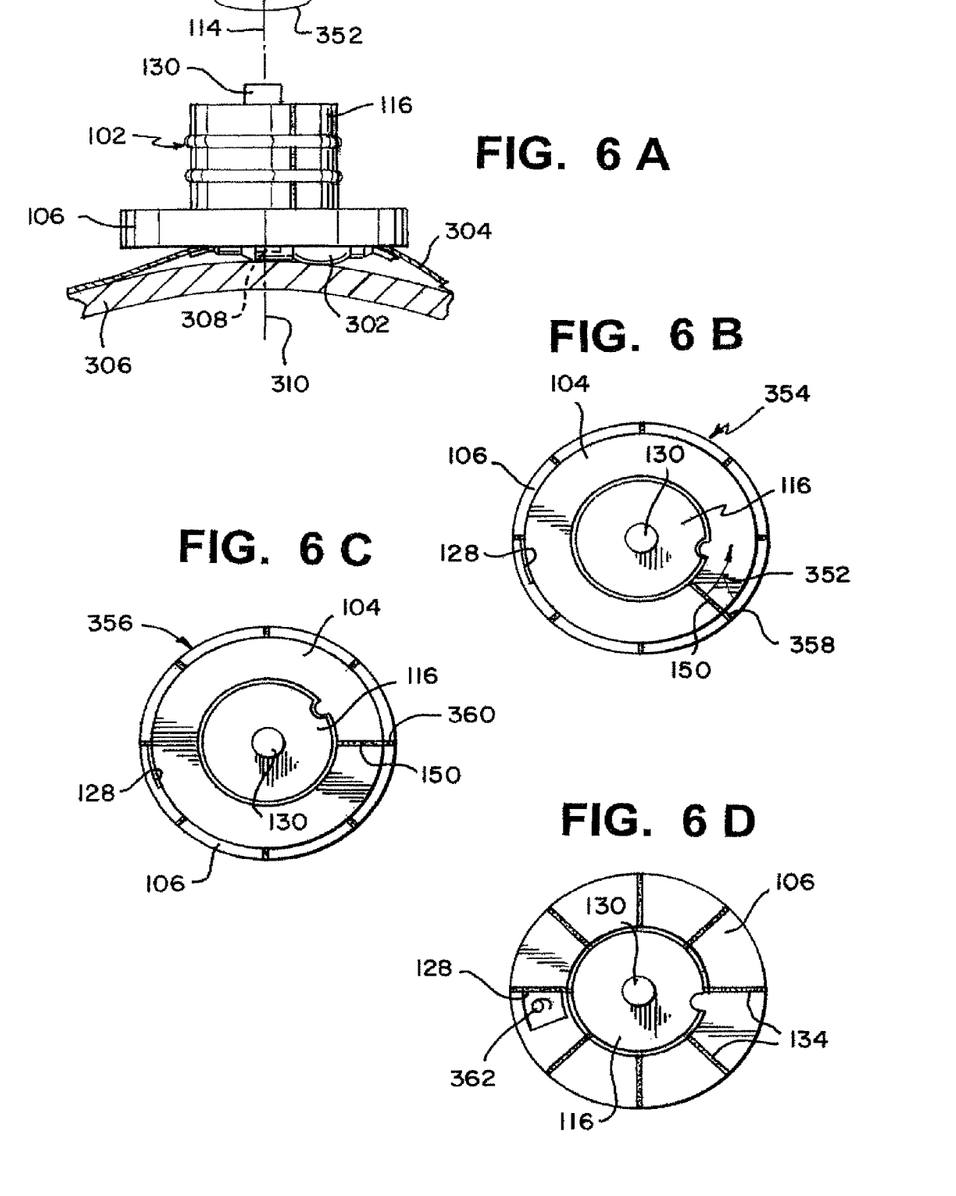

Now referring to FIG. 6a in an adjusting step 330, the adjustor component 104 is seen to have been moved along the tool axis 114 toward and slidingly over the shaft 116, to mount on the locator-indicator component 102. The adjustor component 104 and the disk 124 each has an associated magnetic field, the adjustor component 104 comprising a much stronger magnetic field than the magnetic field of the disk 124. In an embodiment, the reading disk 124 is freed to self-orient to the magnetic field of the adjustor component 104 when these two magnetic elements are in proximity to one another. Strongly magnetic components have the potential to permanently modify the magnetization of more weakly magnetized components positioned nearby. Releasing the disk 124 to magnetically align itself to the magnetic field of the adjustor component 104 helps to protect the disk 124 from such modification by the adjustor component 104. In an embodiment, the adjustor component 104 is mounted to the locator-indicator component 102 for storage between uses of the tool 100. Having the disk 124 thus released during storage further ensures that the magnetization of the disk 124 is preserved for future uses of the tool 100.

In an embodiment, the shaft 116 is rotated about the tool axis 114 with respect to the housing 106 to a rotational orientation corresponding to the valve reading obtained in the locating and indicating steps 320, before the adjustor component 104 is mounted to the locator-indicator component 102. The adjustor component 104 is then rotated about the tool axis 114 to the keyed rotational orientation with respect to the shaft 116, so it will axially fit onto the keyed shaft 116 without further rotation of the adjustor component 104 as the adjustor component approaches the shaft 116. This sequential pre-rotation of the shaft 116 and the adjustor component 104 prevents premature adjustment of the valve 302, or accidental adjustment of the valve 302 to an undesired setting.

It is desirable to avoid unintentional adjustment of the valve 302 due to accidental close approach of the adjustor component 104 to the rotor 308. In an embodiment, the adjustor component 104 cannot adjust the valve 302 unless it is at least as close to the valve 302 as the shaft end 120, when the locator-indicator component 102 is matingly positioned on the scalp 304 above the valve 302. This constraint can be applied in the design of the tool 100 by designing the length of the shaft 116 between the shaft end 120 and the upper surface 108 of the housing 106, and the strength of the magnetic field of the adjustor component 104, such that the strength of the magnetic field of the adjustor component 104 is inadequate to adjust the valve 302 unless the adjustor component 104 is close enough to the rotor 308 so as to be mounted on the shaft 116.

Similarly, the adjustor component 104 can include a minimum external dimension transverse to the tool axis 114 such that, with the locator-indicator component 102 matingly positioned on the scalp 304 over the valve 302, the adjustor component 104 cannot adjust the valve 302 if it is moved toward the valve from the side, for example, parallel to the surface of the scalp 304, at any vertical distance above the scalp 304. In an embodiment, this side-approach is limited by contact between an outside surface of the adjustor component 104 and the outside surface 118 of the shaft 116.

With knowledge of the current valve setting and a target setting, a valve adjustment is performed by rotating the adjustor component 104 in the direction indicated by arrow 352 about the tool axis 114, from the rotational orientation associated with the current valve setting, to a rotational orientation associated with the target setting, guided by one or more of the angular reference markings 134, 136 on the housing 106 of the locator-indicator component 102, and one or more of the angular reference markings 132, 150 on one or both of the shaft 116 and the adjustor component 104.

An embodiment of a valve adjustment from a current valve setting 354 to a target valve setting 356 is illustrated in top views in FIG. 6b and FIG. 6c, respectively. Referring first to FIG. 6b, the adjustor component 104 is seen to be mounted to the locator-indicator component 102, with the alternate visible mark 150 on the adjustor component oriented toward a first one 358 of the radial markings 134 on the housing 106 of the locator-indicator component 102, indicating the current valve setting. To perform the valve adjustment, the adjustor component is manually rotated 352 about the tool axis 114 toward the target setting. Now referring to FIG. 6c, the adjustor component is seen to have been rotated so that the alternate visible mark 150 is now oriented toward a second one 360 of the radial markings 134, indicating the target valve setting.

Once the adjustment has been completed, the adjustor component 104 is demounted from the locator-indicator component 102 by sliding the adjustor component 104 axially along the shaft 116 away from the housing 106. In an embodiment, the valve setting is then verified (read again) as described for the location and indication steps 320, to ensure that the adjustment was performed correctly. FIG. 6d illustrates the verified reading of the valve 302, showing a third one 362 of the plurality of markings 126 on the reading disk 124 visible through the window 128, corresponding to the target setting of the valve 302. Finally, the locator-indicator component 102 is removed from the scalp 304 to complete the procedure.

Advantageously, tools and methods of the present invention provide means to smoothly integrate reading, adjusting, and verifying the setting of an implanted valve in a straightforward, repeatable procedure. In addition, the present invention enables the reading and adjusting of an implantable valve to a target setting with reduced risk of inadvertently or incorrectly adjusting the valve. The reduced risk of misadjustment enhances patient comfort and safety, as inappropriate adjustment could lead to either the overdrainage or underdrainage of CSF, which can result in dangerous conditions, such as subdural hematoma.

Further, two-component tools of the present invention provide several advantages over known tools designed to be used independently to read or to adjust an implanted valve. A first component of the inventive tool matingly fits over the shape of an implanted valve, preferably as palpatable through the patient's scalp, providing reproducible positioning and orientation of the tool, as well as safety and relative comfort for the patient. The same component of the tool provides magnetic reading of the current valve setting without further motion of the patient-contact surface of the tool, additionally enhancing comfort and safety. The first component can also include a releasable lock associated with the reading function, providing stability of the valve reading.

A second component of the tool couples to the first component to adjust the valve, again without further motion of the patient-contact surface of the tool. As a further advantage, the second component of the tool can be decoupled from the first component and the valve setting verified by making an additional reading, before the first component is finally removed from the patient's scalp. In addition to reliability, convenience and safety in use, the coupling of the two tool parts provides convenient storage of the tool as a single unit between uses, while the releasable lock provides protection for the magnetic reading mechanism.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A tool for reading and changing a setting of an implantable valve, the valve having an external cross section and an internal magnetic rotor with an associated magnetic field, the tool comprising:
   a locator-indicator having opposed upper and lower surfaces, a shaft extending from the upper surface, the shaft having a longitudinal axis oriented substantially perpendicular to the upper surface, the lower surface including a biased recess having an internal cross-section matingly complementary to the external cross section of the valve, the biased recess configured to be positioned in proximity to the valve in a unique rotational orientation about the axis, the axis extending through the rotor;
   a magnetic indicator rotatably mounted about the axis between the upper and the lower surface, the indicator being configured to rotate under influence of the magnetic field of the rotor of the valve and into orientation thereto; and
   a magnetic adjustor slidably mountable along the axis onto the shaft, the adjustor having a magnetic field configured to rotate the rotor about the axis in response to rotation of the adjustor about the axis, for changing the setting of the valve.

2. The tool of claim 1 wherein the shaft is rotatably coupled to the upper surface about the axis;
   the shaft and the upper surface being provided with visible markings to identify each of a plurality of rotational orientations between the shaft and the upper surface, the plurality of rotational orientations corresponding to a plurality of valve settings; and
   wherein the adjustor and the shaft are mechanically keyed to rotate together about the axis.

3. The tool of claim 1 wherein the setting of the valve is one of a pressure setting and a flow setting.

4. A tool for reading and changing a current setting of a magnetically readable and settable valve implanted in a patient, the valve having a physical shape and orientation palpatable through the skin of the patient, the tool comprising:
   a) a housing having a lower surface and an upper surface, the lower surface having a complementary shape to the palpatable shape, for fitting thereupon in a predetermined orientation, a shaft rotatably coupled to the upper surface, the shaft having an axis of rotation substantially perpendicular to the upper surface, the shaft having a length along the axis;
   b) a disk at least partially contained within the housing and rotatably mounted about the axis, the disk being magnetically self-aligning to a rotational orientation of the valve indicative of the current setting, when the lower surface is matingly positioned in proximity to the palpatable shape, the disk bearing at least one visible marking indicating the disk's rotational orientation about the axis; and
   c) a magnetic element slidably mountable on the shaft along the axis in a predetermined rotational orientation with respect to the shaft, the magnetic element configured to change the setting of the valve when mounted on the shaft and rotated about the axis along with the shaft.

5. The tool of claim 4 wherein rotation of the magnetic element along with the shaft about the axis generates at least one of a visual, tactile or audible signal when the magnetic element is rotated to any of a predetermined plurality of rotational orientations.

6. The tool of claim 5 wherein the plurality of rotational orientations consists of eight equally spaced orientations.

7. The tool of claim 4 wherein the upper surface includes a window for viewing the at least one marking.

8. The tool of claim 4 further comprising a mechanical lock having a first position in which the disk can rotate freely when subjected to an external magnetic field, and a second position in which the disk is prevented from rotating.

9. The tool of claim 4 wherein the magnetic element is substantially disk-shaped and includes a central aperture for receiving the shaft, the shaft and the magnetic element being mechanically keyed to rotate together when slidingly mated.

10. The tool of claim 4 wherein the magnetic element is capable of changing a setting of the valve only when the magnetic element is positioned at a distance of less the length of the shaft from the upper surface.

11. The tool of claim 4 wherein the magnetic element is capable of changing a setting of the valve only when the magnetic element is mounted on the shaft.

12. The tool of claim 4 wherein the complementary shape comprises a noncircular indentation in the lower surface.

13. A tool for reading and changing a current setting of a magnetically readable and settable valve implanted in a patient, the valve having a physical shape and orientation palpatable through the skin of the patient, the tool comprising:
   a) a housing having a lower surface and an upper surface, the lower surface having a complementary shape to the palpatable shape, for fitting thereupon in a predetermined orientation, a shaft extending from the upper surface, the shaft having an axis substantially perpendicular to the upper surface, the shaft having a length along the axis;
   b) a disk at least partially contained within the housing, the disk including one or more magnets, the disk being rotationally self-aligning to a rotational orientation of the valve, indicative of the current valve setting when the lower surface is matingly positioned in proximity to the palpatable shape; and
   c) a magnetic element slidably mountable on the shaft along the axis, the magnetic element configured to change a setting of the valve when mounted on the shaft and rotated about the axis.

14. The tool of claim 13 wherein at least one of the magnetic element and the housing bear visible markings representative of a setting of the valve.

15. The tool of claim 13 wherein the upper surface includes a window for viewing the rotational orientation of the disk.

16. The tool of claim 13 further comprising a mechanical lock having a first position in which the disk can rotate freely when subjected to an external magnetic field, and a second position in which the disk is prevented from rotating.

17. The tool of claim 13 wherein the magnetic element is substantially disk-shaped and includes a central aperture for receiving the shaft.

18. The tool of claim 13 wherein the magnetic element is capable of changing a setting of the valve only when the magnetic element is positioned at a distance of less the length of the shaft from the upper surface.

19. The tool of claim 13 wherein the magnetic element is capable of changing a setting of the valve only when the magnetic element is mounted on the shaft.

20. The tool of claim 13 wherein the complementary shape comprises a noncircular indentation in the lower surface.

21. A method for reading and changing a current setting of a magnetically readable and settable valve implanted in a patient, the valve having a physical shape and orientation palpatable through the skin of the patient, the method comprising:
   a) providing a first tool portion having an upper surface and a lower surface, the lower surface adapted to matingly fit in proximity to the palpatable shape on the patient, the first portion including a magnetic indicator that magnetically aligns with the valve to indicate the current setting of the valve, a shaft extending from the upper surface, the shaft having an axis;
   b) positioning the first portion matingly in proximity to the palpatable shape on the patient, the shaft extending in a direction substantially away from the patient;
   c) reading the current setting using the magnetic indicator;
   d) providing a second tool portion, the second tool portion adapted to removably slide over the shaft to mate with the first portion, the second portion including a magnet adapted to change the setting of the valve when the second portion is rotated about the axis;
   e) sliding the second portion over the shaft along the axis to mate the second portion with the first portion; and
   f) rotating the second portion about the axis to change the setting of the valve.

22. The method of claim 21 further comprising removing the second portion from the first portion and reading the valve setting to verify a change in the valve setting.

23. A tool for reading and changing a current setting of a magnetically readable and settable valve implanted in a patient, the valve having a physical shape and orientation palpatable through the skin of the patient, the tool comprising:
   a) a first tool portion having an upper surface and a lower surface, the lower surface adapted to matingly fit on the patient in proximity to the palpatable shape, the first portion including a magnetic indicator that magnetically aligns with the valve to indicate the current setting of the valve, a shaft extending from the upper surface, the shaft having an axis;
   b) a second tool portion adapted to removably slide over the shaft to mate with the first portion, the second portion including a magnet adapted to change the setting of the valve when the second portion is rotated about the axis, when the second portion is mounted on the first portion.

24. The tool of claim 23 wherein the magnetic element is substantially disk-shaped and includes a central aperture for receiving the shaft.

25. The tool of claim 24 wherein the shaft and the magnetic element are mechanically keyed to rotate together when slidingly mated together, and wherein shaft is rotationally coupled to the upper surface.

* * * * *